(12) United States Patent
Bruchman et al.

(10) Patent No.: US 10,285,808 B2
(45) Date of Patent: May 14, 2019

(54) EVERTING TRANSCATHETER VALVE AND METHODS

(71) Applicant: W. L. Gore & Associates, Inc., Newark, DE (US)

(72) Inventors: William C. Bruchman, Camp Verde, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 275 days.

(21) Appl. No.: 15/042,351

(22) Filed: Feb. 12, 2016

(65) Prior Publication Data

US 2016/0157998 A1     Jun. 9, 2016

Related U.S. Application Data

(62) Division of application No. 13/797,633, filed on Mar. 12, 2013, now Pat. No. 9,283,072.

(Continued)

(51) Int. Cl.
    *A61F 2/24*            (2006.01)
    *A61L 31/02*        (2006.01)
    (Continued)

(52) U.S. Cl.
    CPC .............. *A61F 2/2403* (2013.01); *A61F 2/24* (2013.01); *A61F 2/2409* (2013.01); *A61F 2/2415* (2013.01); *A61F 2/2418* (2013.01); *A61F 2/2427* (2013.01); *A61F 2/2433* (2013.01); *A61L 31/022* (2013.01); *A61L 31/048* (2013.01); *A61F 2002/9583* (2013.01); *A61F 2210/0076* (2013.01); *A61F 2230/0054* (2013.01); *A61L 2400/16* (2013.01); *A61L 2430/20* (2013.01); *B29C 53/44* (2013.01);
    (Continued)

(58) Field of Classification Search
    CPC ........ A61F 2/24; A61F 2/2403; A61F 2/2409; A61F 2/2427; A61F 2/9587; A61F 2/2415
    See application file for complete search history.

(56) References Cited

U.S. PATENT DOCUMENTS 3,953,566 A    4/1976   Gore
4,178,639 A    12/1979   Bokros
(Continued)

FOREIGN PATENT DOCUMENTS

CN        102764169 A    11/2012
EP         2359774 B1     8/2011
(Continued)

OTHER PUBLICATIONS

International Search Report and Written Opinion of PCT/US2013/046389, dated Jan. 21, 2014, 18 pages.
(Continued)

*Primary Examiner* — Victor Nguyen

(57) ABSTRACT

Described embodiments are directed toward centrally-opening, leaflet valve devices and systems for transcatheter delivery having a two-piece valve body as well as methods of making and delivering the two-piece valve devices. A transcatheter valve includes a collapsed configuration and an expanded configuration. The transcatheter valve can further include an everted configuration and a non-everted configuration.

40 Claims, 11 Drawing Sheets

Related U.S. Application Data

(60) Provisional application No. 61/675,744, filed on Jul. 25, 2012.

(51) Int. Cl.
*A61L 31/04* (2006.01)
*A61F 2/958* (2013.01)
*B29D 23/00* (2006.01)
*B29C 53/44* (2006.01)

(52) U.S. Cl.
CPC ....... *B29D 23/001* (2013.01); *Y10T 29/49405* (2015.01)

(56) References Cited

U.S. PATENT DOCUMENTS

| | | | |
|---|---|---|---|
| 4,265,694 A | 5/1981 | Boretos et al. | |
| 4,477,930 A | 10/1984 | Totten et al. | |
| 5,628,791 A | 5/1997 | Bokros et al. | |
| 5,708,044 A | 1/1998 | Branca | |
| 6,174,331 B1 | 1/2001 | Moe et al. | |
| 6,283,994 B1 | 9/2001 | Moe et al. | |
| 6,283,995 B1 | 9/2001 | Moe et al. | |
| 6,287,334 B1 | 9/2001 | Moll et al. | |
| 6,328,763 B1 | 12/2001 | Love et al. | |
| 6,454,798 B1 | 9/2002 | Moe | |
| 6,482,228 B1 | 11/2002 | Norred | |
| 6,541,589 B1 | 4/2003 | Baillie | |
| 6,562,069 B2 | 5/2003 | Cai | |
| 6,613,086 B1 | 9/2003 | Moe et al. | |
| 6,666,885 B2 | 12/2003 | Moe | |
| 6,916,338 B2 | 7/2005 | Speziali | |
| 6,953,332 B1 | 10/2005 | Kurk et al. | |
| 7,306,729 B2 | 12/2007 | Bacino et al. | |
| 7,381,218 B2 | 6/2008 | Schreck | |
| 7,462,675 B2 | 12/2008 | Chang et al. | |
| 7,510,575 B2 | 3/2009 | Spenser et al. | |
| 7,531,611 B2 | 5/2009 | Sabol et al. | |
| 7,708,775 B2 | 5/2010 | Rowe et al. | |
| 7,780,725 B2 | 8/2010 | Haug et al. | |
| 7,967,853 B2 | 6/2011 | Eidenschink et al. | |
| 7,993,394 B2 | 8/2011 | Hariton et al. | |
| 8,637,144 B2 | 1/2014 | Ford | |
| 8,728,154 B2 | 5/2014 | Alkhatib | |
| 8,870,948 B1 | 10/2014 | Erzberger et al. | |
| 8,961,599 B2 | 2/2015 | Bruchman et al. | |
| 9,101,469 B2 | 8/2015 | Bruchman et al. | |
| 9,139,669 B2 | 9/2015 | Xu et al. | |
| 9,144,492 B2 | 9/2015 | Bruchman et al. | |
| 9,283,072 B2 | 3/2016 | Bruchman | |
| 9,398,952 B2 | 7/2016 | Bruchman et al. | |
| 9,737,398 B2 | 8/2017 | Bruchman et al. | |
| 9,743,932 B2 | 8/2017 | Amplatz et al. | |
| 9,968,443 B2 | 5/2018 | Bruchman et al. | |
| 2002/0082687 A1 | 6/2002 | Moe | |
| 2003/0114913 A1 | 6/2003 | Spenser et al. | |
| 2004/0024448 A1 | 2/2004 | Chang et al. | |
| 2004/0039436 A1 | 2/2004 | Spenser et al. | |
| 2004/0243222 A1 | 12/2004 | Osborne et al. | |
| 2005/0027348 A1 | 2/2005 | Case et al. | |
| 2005/0137682 A1 | 6/2005 | Justino | |
| 2006/0122693 A1 | 6/2006 | Biadillah et al. | |
| 2006/0290027 A1 | 12/2006 | O'Connor et al. | |
| 2007/0010876 A1 | 1/2007 | Salahieh et al. | |
| 2007/0021826 A1 | 1/2007 | Case et al. | |
| 2007/0207186 A1 | 9/2007 | Scanlon et al. | |
| 2008/0009940 A1 | 1/2008 | Cribier | |
| 2008/0065198 A1 | 3/2008 | Quintessenza | |
| 2008/0133004 A1 | 6/2008 | White | |
| 2008/0195199 A1* | 8/2008 | Kheradvar | A61F 2/2418 623/2.11 |
| 2008/0208327 A1 | 8/2008 | Rowe | |
| 2008/0220041 A1 | 9/2008 | Brito et al. | |
| 2009/0157175 A1 | 6/2009 | Benichou | |
| 2009/0240320 A1 | 9/2009 | Tuval et al. | |
| 2009/0264997 A1 | 10/2009 | Salahieh et al. | |
| 2010/0036021 A1 | 2/2010 | Lee et al. | |
| 2010/0082094 A1 | 4/2010 | Quadri et al. | |
| 2010/0137998 A1 | 6/2010 | Sobrino-Serrano et al. | |
| 2010/0168839 A1 | 7/2010 | Braido et al. | |
| 2010/0185274 A1 | 7/2010 | Moaddeb et al. | |
| 2010/0191320 A1 | 7/2010 | Straubinger et al. | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0262231 A1 | 10/2010 | Tuval et al. | |
| 2011/0054515 A1 | 3/2011 | Bridgeman et al. | |
| 2011/0208283 A1 | 8/2011 | Rust | |
| 2011/0218619 A1 | 9/2011 | Benichou et al. | |
| 2011/0251678 A1 | 10/2011 | Eidenschink et al. | |
| 2011/0257739 A1 | 10/2011 | Corbett | |
| 2012/0078357 A1 | 3/2012 | Conklin | |
| 2012/0083839 A1 | 4/2012 | Letac et al. | |
| 2012/0101567 A1 | 4/2012 | Jansen | |
| 2012/0101571 A1 | 4/2012 | Thambar et al. | |
| 2012/0130471 A1 | 5/2012 | Shoemaker et al. | |
| 2012/0185038 A1* | 7/2012 | Fish | A61F 2/2415 623/2.13 |
| 2012/0323315 A1 | 12/2012 | Bruchman et al. | |
| 2014/0031924 A1 | 1/2014 | Bruchman et al. | |
| 2014/0031927 A1 | 1/2014 | Bruchman et al. | |
| 2014/0172078 A1 | 6/2014 | Bruchman et al. | |
| 2014/0172083 A1 | 6/2014 | Bruchman et al. | |
| 2014/0180400 A1 | 6/2014 | Bruchman et al. | |
| 2014/0236289 A1 | 8/2014 | Alkhatib | |
| 2014/0324164 A1* | 10/2014 | Gross | A61F 2/2409 623/2.37 |
| 2015/0142100 A1 | 5/2015 | Morriss | |
| 2016/0157998 A1 | 6/2016 | Bruchman | |

FOREIGN PATENT DOCUMENTS

| | | |
|---|---|---|
| FR | 2591100 | 6/1987 |
| GB | 2312485 | 10/1997 |
| JP | 196932400 B | 12/1969 |
| JP | 2012152563 A | 8/2012 |
| WO | 1996002212 A1 | 2/1996 |
| WO | WO-0062716 | 10/2000 |
| WO | 2006108090 A2 | 10/2006 |
| WO | WO2008097589 A1 | 8/2008 |
| WO | WO-2008097592 | 8/2008 |
| WO | WO2009029199 A1 | 3/2009 |
| WO | 2010057262 A8 | 5/2010 |
| WO | 2011112706 A2 | 9/2011 |
| WO | WO-2011/109450 A2 | 9/2011 |
| WO | WO-2011109801 | 9/2011 |
| WO | 2012040643 A2 | 3/2012 |
| WO | WO-2012082952 | 6/2012 |
| WO | WO-2012110767 | 8/2012 |
| WO | WO-2012167131 | 12/2012 |
| WO | WO-2014018432 | 1/2014 |

OTHER PUBLICATIONS

European Search Report from EP16196687.4, dated Nov. 21, 2017, 5 pages.
Clough, Norman E. Introducing a New Family of GORE ePTFE Fibers (2007), pp. 1-10.
International Search Report for PCT/US2013/051431 dated Jan. 20, 2014, corresponding to U.S. Appl. No. 13/797,526; 6 pages.
International Search Report for PCT/US2013/068390 dated Apr. 29, 2014, corresponding to U.S. Appl. No. 13/835,988, 7 pages.
International Search Report for PCT/US2013/068780 dated Feb. 27, 2014, corresponding to U.S. Appl. No. 13/869,878, 4 pages.
International Search Report for PCT/US2013/071632 dated Apr. 28, 2014, corresponding to U.S. Appl. No. 13/841,334, 6 pages.
International Search Report for PCT/US2013/074962 dated Feb. 27, 2014, 4 pages.
International Search Report for PCT/US2013/075274 dated Feb. 27, 2014, corresponding to U.S. Appl. No. 13/843,196, 5 pages.
International Search Report for PCT/US2013/075380 dated Mar. 6, 2014, 5 pages.

(56) References Cited

OTHER PUBLICATIONS

International Search Report for PCT/US2013/076504 dated Apr. 28, 2014, corresponding to U.S. Appl. No. 14/133,491, 7 pages.
International Search Report for PCT/US2013/076688 dated Feb. 27, 2014, 5 pages.

* cited by examiner

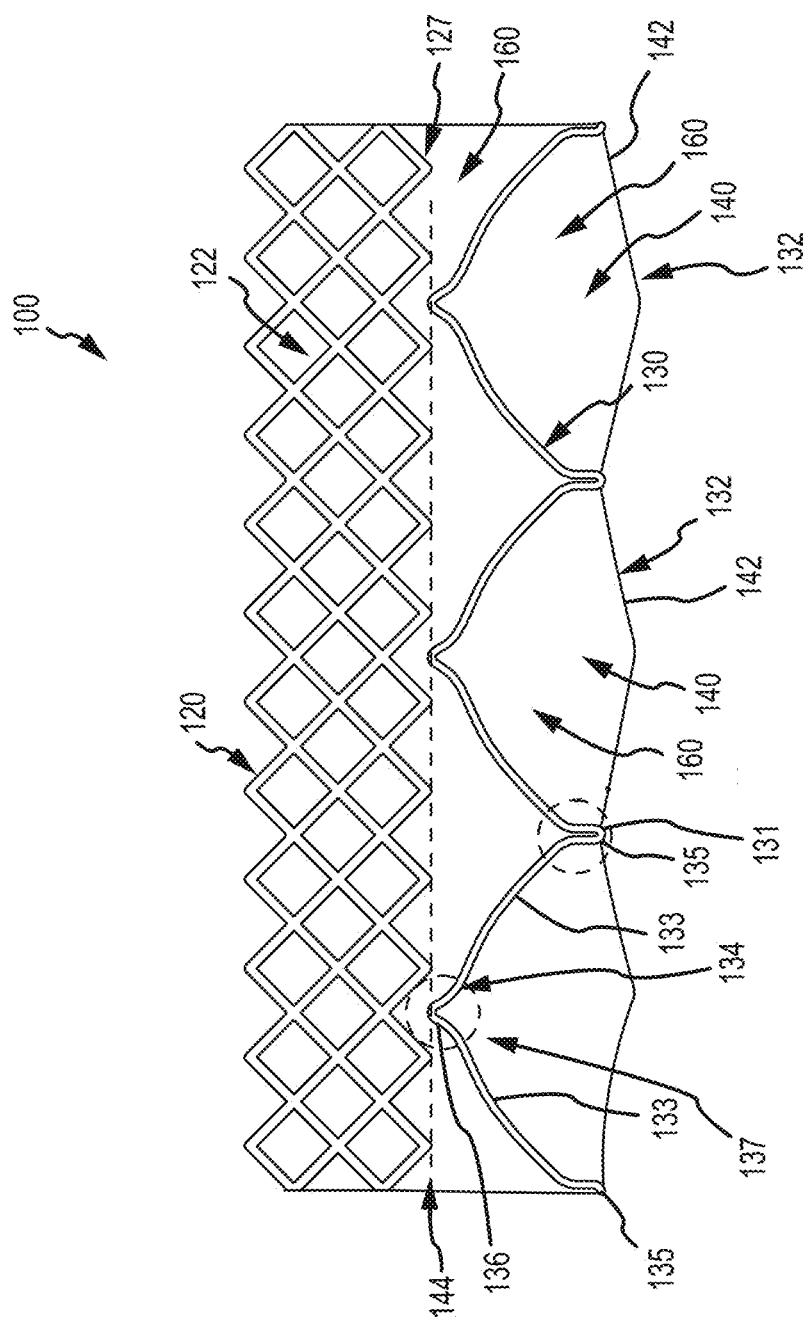

EVERTING TRANSCATHETER VALVE AND METHODS

CROSS-REFERENCE TO RELATED APPLICATIONS

This application is a divisional of U.S. patent application Ser. No. 13/797,633, filed Mar. 12, 2013 entitled EVERTING TRANSCATHETER VALVE AND METHODS, which claims priority to provisional application Ser. No. 61/675,744 filed Jul. 25, 2012, entitled EVERTING TRANSCATHETER VALVE AND METHODS, which are herein incorporated by reference in their entirety.

FIELD

The present disclosure relates generally to prosthetic valves and more specifically leaflet-type prosthetic valve devices, systems, and methods for transcatheter delivery.

BACKGROUND

A transcatheter prosthetic valve that can be delivered endovascularly via a catheter can help to minimize patient trauma as compared with an open-heart, surgical procedure. Open heart surgery involves extensive trauma to the patient, with attendant morbidity and extended recovery. A valve delivered to the recipient site via a catheter avoids the trauma of open heart surgery and may be performed on patients too ill or feeble to survive the open heart surgery.

Transcatheter valve implantation with currently available transcatheter valves and associated delivery catheters, together referred herein as delivery systems, present several procedural-related complications. Trauma to the peripheral vasculature as well as dissection of the ascending and descending aorta has been observed. This trauma is associated, in part, with the relatively large diameter of the delivery systems. Minimizing such trauma can be facilitated by minimizing the diameter of the delivery system which is determined, in part, by the profile of the valve on the associated delivery catheter.

Reducing the profile of the prosthetic heart valve on the delivery catheter is technically challenging. For example, a 23 mm diameter aortic prosthetic valve might have to be advanced through 10 mm diameter vasculature to reach the deployment site. This requires that the valve be compressed to a smaller diameter upon the delivery catheter such that it and the delivery catheter present a diameter somewhat smaller than 10 mm.

The profile of the valve is dependent, in part, on the valve components. Some transcatheter valve devices comprise a valve having flexible leaflets mounted inside a tubular metal frame. The metal frame may be self expanding or balloon-expanded from a pre-deployed compressed diameter to the deployed functional diameter. The diameter of the delivery system is dependent, in part, on the resulting thickness of the compressed valve leaflets within the frame as it is mounted on the delivery catheter.

The transcatheter valve must be capable of being securely coupled to the tissue orifice of the implantation site after endovascular placement so as to avoid, for example, dislodgement or migration of the valve after placement. The coupling of the valve to the implantation site is commonly facilitated by relatively high hoop strength of the frame placed in urging engagement with the tissue orifice.

Bioprosthetic valves have been developed that attempt to mimic the function and performance of a native valve. Flexible leaflets are fabricated from biological tissue such as bovine pericardium. In some valve designs the biological tissue is sewn onto a relatively rigid frame that supports the leaflets and provides dimensional stability when implanted. Although bioprosthetic valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic valve, herein referred to as a synthetic leaflet valve (SLV). However, synthetic leaflet valves have not become a valid valve replacement option since they suffer premature failure, due to, among other things, suboptimal design and lack of a durable synthetic material.

A number of fabrication techniques have been used to couple the leaflets to a frame, including sewing individual leaflets to the frame (biological and synthetic), and for synthetic leaflets only, injection molding and dip coating a polymer onto the frame. In each case, the resulting leaflet is supported on the frame and defines a flap having a mounting edge where the leaflet is coupled to the frame and a free edge that allows the flap to move. The flap moves under the influence of fluid pressure. In operation, the leaflets open when the upstream fluid pressure exceeds the downstream fluid pressure and close when the downstream fluid pressure exceeds the upstream fluid pressure. The free edges of the leaflets coapt under the influence of downstream fluid pressure closing the valve to prevent downstream blood from flowing retrograde through the valve.

Valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material. Mechanical failure at the mounting edge is especially prevalent with synthetic leaflets.

There exists a need for a durable transcatheter prosthetic valve that is compressible to a small diameter and capable of being delivered endovascularly.

SUMMARY

Described embodiments are directed to an apparatus, system, and methods for valve replacement, such as cardiac valve replacement. More specifically, described embodiments are directed toward flexible leaflet valve devices and systems having a multi-part support member or frame, and methods of making and delivering the valve devices.

According to an embodiment, a valve comprises a leaflet frame, a body frame, and any number of leaflets suitable for the size and function of the valve, having a collapsed configuration and an expanded configuration. In a further embodiment, the valve can comprise an everted configuration and a non-everted configuration.

According to an embodiment, a transcatheter valve comprising a body frame and a leaflet frame coupled by a film is provided. The body frame has a generally tubular shape defining a body frame lumen. The leaflet frame has a generally annular shape defining a plurality of U-shaped portions each defining a base and a plurality of posts. The body frame extends coaxially, adjacent to and spaced apart from the leaflet frame. The base of each U-shaped portion being located proximate to but not in contact with a body frame first end of the body frame with the U-shaped portions of the leaflet frame extending away from the body frame and the posts extending away from body frame, the posts being distal from the body frame first end. The film extends across and between the U-shaped portions and the body frame. The film that extends between the body frame and the leaflet frame defines a fold region. The film that extends across each of the U-shaped portions defines a leaflet. The leaflet frame is operable to evert to an everted position by rotating about the fold region to a position in which the leaflet frame is at least partially coaxially disposed at least partially within the body frame lumen, wherein each leaflet is moveable between an open and closed position.

According to an embodiment, a transcatheter valve comprising a body frame and a leaflet frame coupled by a film is provided. The body frame defines a generally tubular shape. The leaflet frame defines a generally annular shape. The leaflet frame is coaxially disposed relative to the body frame, extending away and spaced apart from the body frame defining a fold region therebetween. The leaflet frame defines a plurality of U-shaped portions each defining a base and a plurality of posts. The base of each U-shaped portion being located proximate to but not in contact with a body frame first end of the body frame with the U-shaped portions of the leaflet frame extending away from the body frame and the posts extending away from body frame, the posts being distal from the body frame first end. The film extends across and between the body frame and leaflet frame bridging the fold region and coupling the body frame to the leaflet frame. The leaflet frame and film defines a plurality of leaflets disposed within each U-shaped portion, each leaflet having a leaflet free edge. The leaflet frame is operable to evert along the fold region so as to dispose the leaflet frame at least partially within the body frame and defining a valve wherein the leaflet free edges abut adjacent leaflet free edges and are moveable between an open and closed position.

According to an embodiment, a transcatheter valve delivery system comprising a delivery catheter, and a transcatheter valve having a body frame and a leaflet frame coupled by a film is provided. The body frame has a generally tubular shape defining a body frame lumen. The leaflet frame has a generally annular shape defining a plurality of U-shaped portions each defining a base and a plurality of posts. The body frame extends coaxially, adjacent to and spaced apart from the leaflet frame. The base of each U-shaped portion being located proximate to but not in contact with a body frame first end of the body frame with the U-shaped portions of the leaflet frame extending away from the body frame and the posts extending away from body frame, the posts being distal from the body frame first end. The film extends across and between the U-shaped portions and the body frame. The film that extends between the body frame and the leaflet frame defines a fold region. The film that extends across each of the U-shaped portions defines a leaflet. The leaflet frame is operable to evert to an everted position by rotating about the fold region to a position in which the leaflet frame is at least partially coaxially disposed at least partially within the body frame lumen, wherein each leaflet is moveable between an open and closed position. The transcatheter valve comprises a collapsed configuration and an expanded configuration. The delivery catheter is operable to advance the transcatheter valve to an implantation site.

According to another embodiment, a transcatheter valve replacement system comprises a valve having a leaflet frame, a body frame, and any number of leaflets, wherein the valve comprises a collapsed configuration and an expanded configuration, and a catheter. The system can further comprise an everting device to transition the valve from an everted configuration to a non-everted configuration.

According to another embodiment, a method of making a transcatheter valve comprises the steps of coupling a leaflet frame and a body frame with a biocompatible material as described herein, either simultaneously or sequentially, and thereby also forming leaflets.

Other methods can comprise delivering, via an intravascular procedure, a transcatheter valve comprising a leaflet frame, a body frame, and any number of leaflets and having a collapsed configuration and an expanded configuration. The method can comprise everting the valve once the transcatheter valve is at its implantation site.

According to another embodiment, a method of delivery of a transcatheter valve comprises loading a transcatheter valve in a collapsed configuration onto a distal section of an elongated flexible catheter having proximal and distal ends, delivering the transcatheter valve to a native valve orifice intravascularly, expanding the transcatheter valve into a native orifice, and everting the leaflet frame into the body frame lumen of the transcatheter valve. The transcatheter valve comprises a body frame and a leaflet frame coupled by a film is provided. The body frame has a generally tubular shape defining a body frame lumen. The leaflet frame has a generally annular shape defining a plurality of U-shaped portions each defining a base and a plurality of posts. The body frame extends coaxially, adjacent to and spaced apart from the leaflet frame. The base of each U-shaped portion being located proximate to but not in contact with a body frame first end of the body frame with the U-shaped portions of the leaflet frame extending away from the body frame and the posts extending away from body frame, the posts being distal from the body frame first end. The film extends across and between the U-shaped portions and the body frame. The film that extends between the body frame and the leaflet frame defines a fold region. The film that extends across each of the U-shaped portions defines a leaflet. The leaflet frame is operable to evert to an everted position by rotating about the fold region to a position in which the leaflet frame is at least partially coaxially disposed at least partially within the body frame lumen, wherein each leaflet is moveable between an open and closed position.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 2 is a representation of the embodiment of the two piece valve of FIG. 1A unrolled to a flat orientation;

DETAILED DESCRIPTION

Figures 1A, 1B:
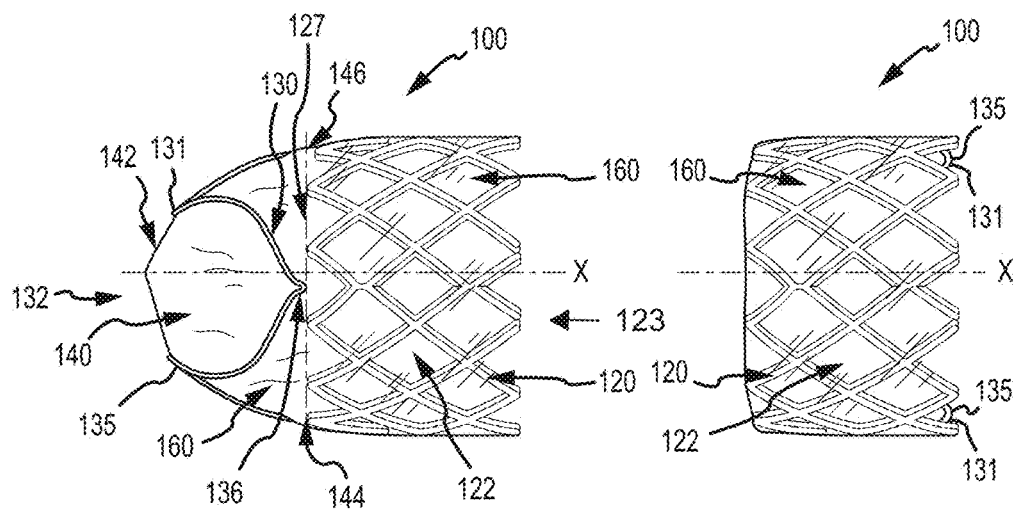
FIG. 1A is a side view of an embodiment of a two piece valve in a non-everted configuration.
FIG. 1B is a side view of the embodiment of the two piece valve of FIG. 1A in an everted configuration.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets opens and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to a film or a biological material, such as, but not limited to, bovine pericardium.

The terms evert, everting, everted, eversion, and evertable as used herein refer to the act, condition, or ability of being turned inside out by folding inward. As used herein, a leaflet frame extends away from a body frame in a non-everted condition, wherein the leaflet frame may be everted by folding the leaflet frame inward such that it extends at least partially into the body frame.

The terms native valve orifice and tissue orifice refers to an anatomical structure into which a prosthetic valve may be placed. Such anatomical structure includes, but is not limited to, a location wherein a cardiac valve may or may not have been surgically removed. It is understood that other anatomical structures that may receive a prosthetic valve include, but are not limited to, veins, arteries, ducts and shunts. Although reference is made herein to replacing a native valve with a prosthetic valve, it is understood and appreciated that a valve orifice or implant site may also refer to a location in a synthetic or biological conduit that may receive a valve for a particular purpose, and therefore the scope of the embodiments provided herein is not limited to valve replacement.

As used herein, "couple" means to join, couple, connect, attach, adhere, affix, or bond, whether directly or indirectly, and whether permanently or temporarily.

Embodiments herein include various apparatus, systems, and methods for a prosthetic valve suitable for transcatheter placement, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

In accordance with embodiments the valve is operable to have a pre-deployed configuration where the valve leaflets are carried by a leaflet frame that is external to a body frame and a post-deployed configuration wherein the leaflet frame is everted into the body frame presenting the leaflets inside the body frame. This allows for greater radial compression of the valve to a smaller diameter during delivery as compared to a configuration wherein the leaflet frame and leaflets are within the body frame.

Further, each of the body frame and leaflet frame may have different physical properties suitable for a particular purpose. In accordance with embodiments, the body frame may be relatively stiff so as to abut and fixedly engage the tissue orifice as well as provide dimensional stability to the valve. The leaflet frame may be relatively less stiff relative to the body frame. The benefit of the leaflet frame being relatively less stiff relative to the body frame may be to slow down the rate of loading on the leaflets to reduce the stress levels on the leaflets whereby improving valve durability. Stiff and stiffness, as used herein and as is commonly used in engineering, is a measure of the resistance to deformation given by a body. Stiff and stiffness is a function of, among other things, material properties, the shape of the object, and the boundary conditions on the object. Stiffness of the leaflet frame 130 (see FIG. 1C) may be measured by any number of methods known in the art. In accordance with one method, cables may be coupled to each of the three posts 131 and brought together so as to allow the cables to be pulled simultaneously along the axis of the leaflet frame, with the leaflet frame restrained about the flex points 136 or as held by the body frame 120. The amount of force on the cables required to deflect the three posts toward the axis provides a measure of stiffness. The same may be done with the body frame 120 with the cables coupled to three equally spaced points on the body frame 120, such as an apex of the diamond-shaped apertures 120 opposite from the fold region 144. The stiffness measurement may be performed in the un-everted configuration (see FIG. 1A) or everted configuration (see FIG. 1B).

In accordance with embodiments the valve comprises means for ensuring that the leaflet frame is accurately and reliably indexed and aligned within the body frame. This is accomplished by virtue of elements that provide for the capability of everting the leaflet frame into the body frame as well and in addition to alignment elements.

The Valve

Figure 1C:
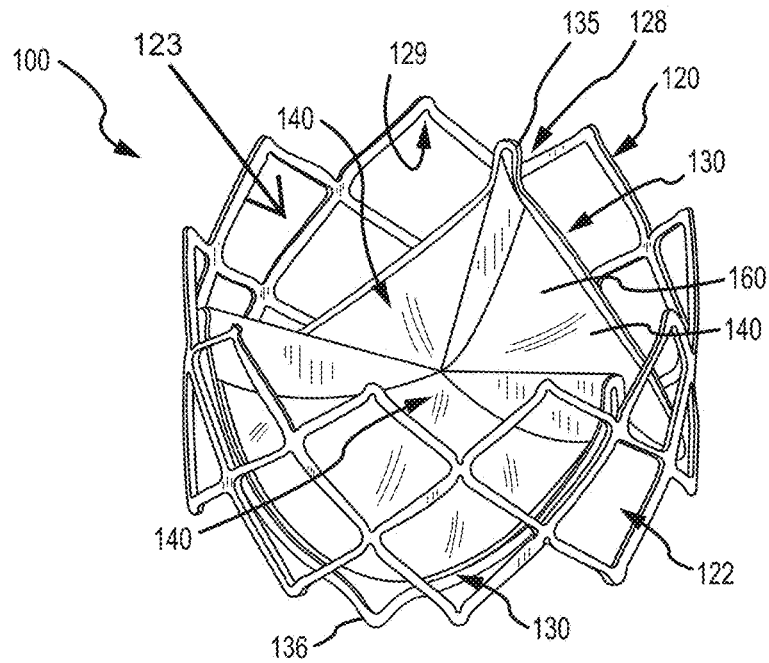
FIG. 1C is a perspective view of the embodiment of the two piece valve of FIG. 1A in an everted configuration.
Figure 3A:
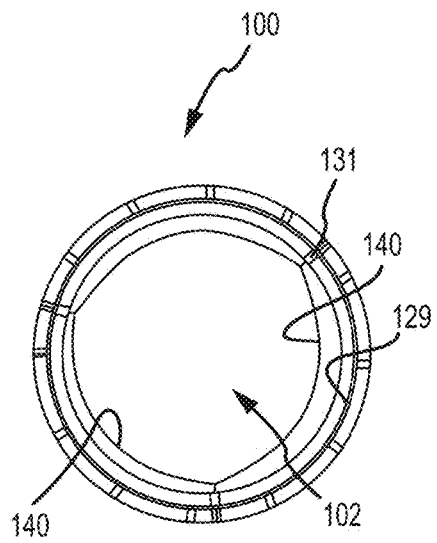
FIG. 3A is an axial view of the embodiment of the two piece valve of FIG. 1A in an open configuration.
Figure 3B:
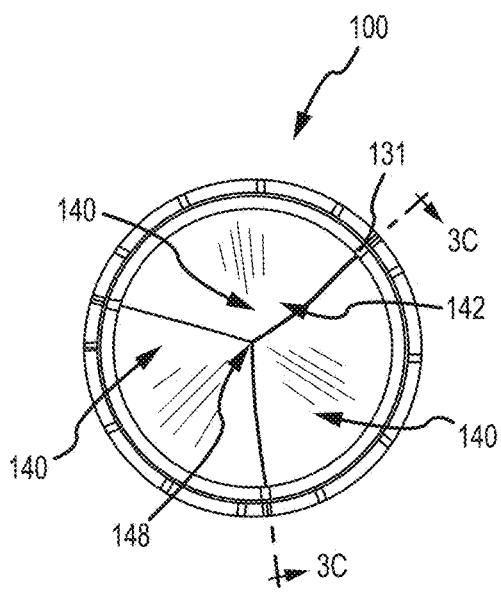
FIG. 3B is a side view of the embodiment of the two piece valve of FIG. 1A in a closed configuration.

FIGS. 1A-1B are side views of a valve 100 in a non-everted and everted configuration, respectively, in accordance with an embodiment. FIG. 1C is a perspective view of the embodiment of FIG. 1B. FIG. 2 illustrates the embodiment of FIG. 1A wherein the valve 100 has been longitudinally cut and laid open to better illustrate the elements of the generally tubular-shaped valve 100. FIGS. 3A and 3B are axial views of the valve 100 in an open and closed configuration, respectively. The valve 100 comprises a body frame 120, a leaflet frame 130, and a film 160 covering the body frame 120 and leaflet frame 130, coupling the body frame 120 to the leaflet frame 130, and defining leaflets 140.

The Film

The film 160 is generally any sheet-like material that is biologically compatible and configured to couple to the body frame 120 and the leaflet frame 130. The leaflets 140 are also comprised of the film 160. It is understood that the film 160 is used generically for one or more biocompatible materials suitable for a particular purpose. It is also understood that the film 160 coupled to the body frame 120 may not be the same film 160 coupled to the leaflet frame 130. Details of various types of film are discussed below. In an embodiment, the film 160 may be formed from a generally tubular material to at least partially cover the body frame 120 and the leaflet frame 130. The film 160 can comprise one or more of a membrane, composite material, or laminate. Details of various types of film 160 are discussed below.

The Body Frame

The body frame 120 is a generally tubular member defining a body frame lumen 123 having a body frame inner surface 129, as shown in FIGS. 1A, 1C, and 3A. The body frame 120 defines a generally open pattern of apertures 122 operable to allow the body frame 120 to be compressed and expanded between different diameters. The body frame 120 may comprise a structure known in the art as a stent. A stent is a tubular member that may have a small diameter suitable for percutaneous transcatheter delivery into the anatomy, and may be expanded to a larger diameter when deployed into the anatomy. Stents having various designs and material properties are well known in the art.

Figure 1D:
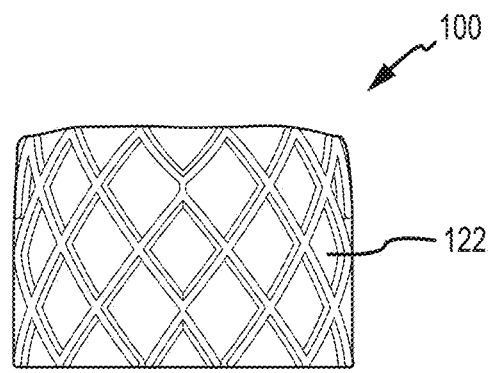
FIG. 1D is a representation of a valve in an expanded configuration.
Figure 1E:
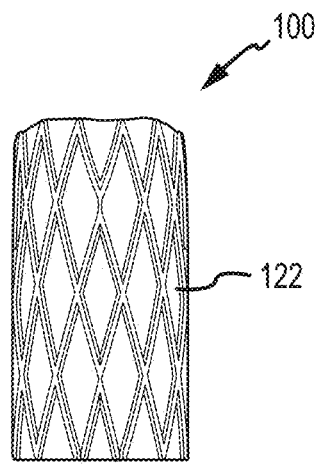
FIG. 1E is a representation of a valve in a compressed configuration.

By way of example, and as illustrated in the embodiments of FIGS. 1A-1C and 2, the valve 100 includes the body frame 120 that defines a stent having apertures 122 having a generally square diamond-shape when in a large diameter configuration, as shown in FIG. 1D. Upon compression to a smaller diameter, the apertures 122 deform to generally define an elongated diamond shape, as shown in FIG. 1E. Upon re-expansion to a larger diameter, the apertures 122 re-expand to again define a generally square diamond shape.

An open framework of the stent can define any number of features, repeatable or otherwise, such as geometric shapes and/or linear or meandering series of sinusoids. Geometric shapes can comprise any shape that facilitates substantially uniform circumferential compression and expansion. An open framework can be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

It is known that stents of various designs may be elastically deformable so as to be self-expanding under spring loads. It is also known that stents of various designs may be plastically deformable so as to be mechanically expanded such as with a balloon. It is also known that stents of various designs may be plastically deformable as well as elastically deformable. The embodiments of the body frame 120 presented herein are not to be limited to a specific stent design or mode of expansion.

The body frame 120 can comprise any metallic or polymeric material. For example, the body frame 120 can comprise a material, such as, but not limited to nitinol, cobalt-nickel alloy, stainless steel, or polypropylene, acetyl homopolymer, acetyl copolymer, ePTFE, other alloys or polymers, or any other material that is generally biocompatible having adequate physical and mechanical properties to function as described herein.

Figure 4:
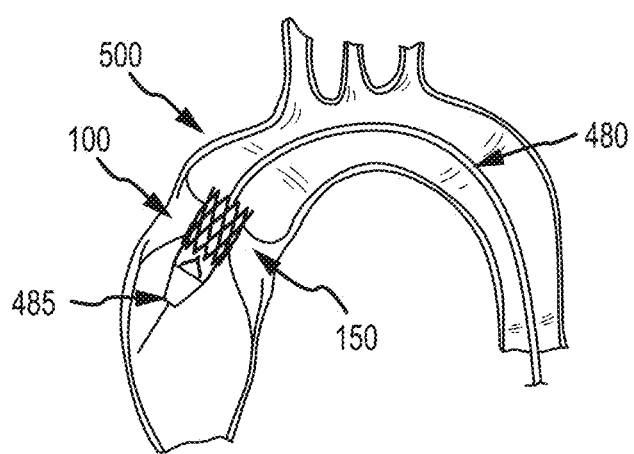
FIG. 4 is a side view of an embodiment of a delivery system within anatomy.

In accordance with embodiments, the body frame 120 can be configured to provide positive engagement with an implant site to firmly anchor the valve 100 to the site, as shown in FIG. 4. In accordance with an embodiment, the body frame 120 can comprise a sufficiently rigid frame having small elastic recoil so as to maintain sufficient apposition against a tissue orifice 150 to maintain position. In accordance with another embodiment, the body frame 120 can be configured to expand to a diameter that is larger than a tissue orifice 150 so that when valve 100 expands into the tissue orifice 150, it can be firmly seated therein. In accordance with another embodiment, the body frame 120 can comprise one or more anchors (not shown) configured to engage the implant site, such as a tissue orifice 150, to secure the valve 100 to the implant site.

It is appreciated that other elements or means for coupling the valve 100 to an implant site are anticipated. By way of example, but not limited thereto, other means, such as mechanical and adhesive means may be used to couple the valve 100 to a synthetic or biological conduit.

Leaflet Frame

The leaflet frame 130 comprises a generally annular member defining a predetermined repeating pattern as shown in FIGS. 1A and 2. The leaflet frame 130 may comprise a wire, ribbon, cut tube, or any other element suitable for the particular purpose. As shown in FIG. 2, the leaflet frame 130 comprises three interconnected U-shaped portions 132. Each of the U-shaped portions 132 defines two sides 133 that define a base 134, with each side 133 having a free end 135. In this embodiment, the base 134 defines a flex point 136 which will be described further below. The free end 135 of one U-shaped portion 132 is interconnected with a free end 135 of an adjacent U-shaped portion 132 which define a post 131.

As shown in FIG. 2, the three posts 131 extend away from body frame when in the non-everted configuration.

The leaflet frame 130 is elastically compressible to obtain a relatively small diameter to accommodate percutaneous transcatheter mounting and delivery. In accordance with an embodiment as shown in FIG. 2, the leaflet frame 130 may comprise one or more flex points 136 so as to provide a preferential flexing location for the leaflet frame 130 to flex when compressed to a smaller diameter. A flex point 136 comprises a site on the leaflet frame 130 that undergoes the highest degree of bending when transitioning from an expanded state to collapsed state and visa versa. In accordance with an embodiment, at least one flex point 136 is proximate the post 131, and at least one flex point 136 is proximate the base 134 of the U-shaped portion 132. The flex point 136 can comprise a structural modification or material modification that biases the leaflet frame 130 to bend at the flex point 136 when compressed.

Figure 3C:
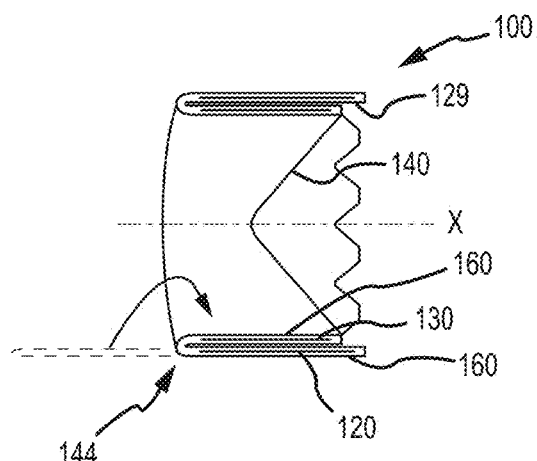
FIG. 3C is a side cross-sectional view of the embodiment of the everted two piece valve of FIG. 1B.

The leaflet frame 130 is elastically deformable so as to allow the leaflet frame 130 to flex when everted from the non-everted extended position, shown in FIG. 1A, to the everted configuration shown in FIG. 3C. In addition, a relatively less stiff leaflet frame 130 supporting the leaflets 140 is more likely to reduce the loading encountered by the opening and closing leaflets 140 as compared to a more stiff leaflet frame 130. The leaflet frame 130 having a relatively less stiff property may reduce leaflet accelerations and reduce the closing stresses on the leaflets 140.

The leaflet frame 130 may comprise, such as, but not limited to, any elastically deformable metallic or polymeric material that is biocompatible. The leaflet frame 130 may comprise a shape-memory material, such as nitinol, a nickel-titanium alloy. Other materials suitable for the leaflet frame 130 include, but are not limited to, other titanium alloys, stainless steel, cobalt-nickel alloy, polypropylene, acetyl homopolymer, acetyl copolymer, other alloys or polymers, or any other material that is generally biocompatible having adequate physical and mechanical properties to function as a leaflet frame 130 as described herein.

In accordance with an embodiment, the leaflet frame 130 comprises a shape memory material operable to flex under load and retain its original shape when the load is removed, thus allowing the leaflet frame 130 to self-expand from a compressed shape to a predetermined shape. The leaflet frame 130 and the body frame 120 may comprise the same or different materials. In accordance with an embodiment, the body frame 120 is plastically deformable to be expanded by a balloon and the leaflet frame 130 is elastically deformable so as to be self-expanding.

Leaflet

Each of the U-shaped portions 132 of the leaflet frame 130 defines an inner region 137. Each inner region 137 is provided with a biocompatible material, such as film 160, which is coupled to the sides 133 and base 134 of the leaflet frame 130 with the film 160 defining a leaflet 140. Each leaflet 140 defines a leaflet free edge 142.

In accordance with an embodiment, the biocompatible material that makes up the leaflet 140 comprises a biological tissue, such as, but not limited to, bovine pericardium. In accordance with other embodiments, the biocompatible material is a film 160 that is not of a biological source and that is sufficiently compliant and strong for the particular purpose, such as a biocompatible polymer. In an embodiment, the leaflet 140 comprises a biocompatible polymer that is combined with an elastomer, referred to as a composite.

The shape of the leaflets 140 are defined in part by the shape of the leaflet frame 130 and the leaflet free edge 142. As will be discussed below in accordance with an embodiment, the shape of the leaflets 140 also depends in part on molding the leaflets 140 using a molding process to impart a predetermined shape to the leaflet 140.

In accordance with an embodiment, in the everted configuration, substantially the entire leaflet frame 130 lies adjacent to the body frame inner surface 129. As such, when the leaflets 140 are in a fully open position, the valve 100 presents a substantially circular valve orifice 102 as shown in FIG. 3A, where the leaflet frame 130 minimally extends into the flow orifice. Fluid flow is permitted through the valve orifice 102 when the leaflets 140 are in an open position.

The leaflets 140 generally flex about the base 134 of the U-shaped portion 132 as the leaflets 140 open and close. When the valve 100 is closed, generally about half of each leaflet free edge 142 abuts an adjacent half of a leaflet free edge 142 of an adjacent leaflet 140, as shown in FIG. 3B. The three leaflets 140 of the embodiment of FIG. 3B meet at a triple point 148. The valve orifice 102 is occluded when the leaflets 140 are in the closed position stopping fluid flow.

The leaflet 140 can be configured to actuate at a pressure differential in the blood caused, for example, by the contraction of a ventricle or atrium of the heart, such pressure differential typically resulting from a fluid pressure building up on one side of the valve 100 when closed. As the pressure on an inflow side of the valve 100 rises above the pressure on the outflow side of the valve 100, the leaflet 140 opens and blood flows therethrough. As blood flows through the valve 100 into a neighboring chamber or blood vessel, the pressure equalizes. As the pressure on the outflow side of the valve 100 rises above the blood pressure on the inflow side of the valve 100, the leaflet 140 returns to the closed position generally preventing the retrograde flow of blood through the inflow side of the valve 140.

It is understood that the leaflet frame 130 may comprise any number of U-shaped portions 132, and thus leaflets 140, suitable for a particular purpose. Leaflet frames 130 comprising one, two, three or more U-shaped portions 132 and corresponding leaflets 140 are anticipated.

Valve Film

As shown in FIG. 1A, the body frame 120 is located coaxially, laterally adjacent to and spaced apart from the leaflet frame 130 and, as shown in FIG. 2, coplanar therewith in the unwrapped view of the valve 100. The base 134 of the U-shaped portion 132 is located proximate to a body frame first end 127 of the body frame 120 with the U-shaped portions 132 of the leaflet frame 130 extending away from the body frame 120. The space between the body frame 120 and the leaflet frame 130 defines a fold region 144 of the valve 100 when bridged with film 160. The valve 100 further comprises a film 160 which is coupled to the body frame 120 and the leaflet frame 130 which couples the body frame 120 to the leaflet frame 130 across at least the fold region 144. As will be discussed below, in the everted configuration, the film 160 is folded along a generally circumferential line 146 in the fold region 144. The film 160 in the fold region 144 provides a hinge about which the leaflet frame 130 may evert into the body frame 120.

It is anticipated that the film 160 may be coupled to the leaflet frame 130 and the body frame 120 in many ways suitable for a particular purpose. By way of example, and not limited thereto, the body frame 120 may be wrapped with overlapping layers of a film 160 having a first composition. The leaflet frame 130 may be wrapped with overlapping layers of a film 160 having a second composition. The wrapped leaflet frame 130 and the wrapped body frame 120 may both be wrapped with overlapping layers of a film 160 having a third composition bridging the fold region 144 between the leaflet frame 130 and the body frame 120.

In another embodiment, the film 160 may be coupled to the inside or outside surface of the leaflet frame 130 and body frame 120. In another embodiment, the film 160 may be coupled to the inside and outside surface of the leaflet frame 130 and body frame 120 sandwiching the leaflet frame 130 and body frame 120 between the film 160.

The film 160 is configured to prevent blood from traveling through or across the valve 100 other than through the valve orifice 102 when the leaflets 140 are in an open position. As such, the film 160 creates a barrier to blood flow in any interstitial space(s) of the body frame 120 and leaflet frame 130, and therebetween, that the film 160 covers.

The film 160 is fixedly secured or otherwise coupled at a single or a plurality of locations of the inside surface or outside surface of the body frame 120 and leaflet frame 130, for example, using one or more of taping, heat shrinking, adhesion and other processes known in the art. In some embodiments, a plurality of membrane/composite layers, i.e., a laminate, are used and can be coupled to both the inner and outer surfaces of the body frame 120 and the leaflet frame 130 to form at least a portion of the film 160.

The film 160 comprises any material(s) that have the suitable physical and mechanical properties to perform the functions described herein. The film 160 may comprise the same material that the leaflet 140 comprises, as described above, or a different material. Similarly, the film 160 may or may not be homogenous in material composition. Different portions of the film 160 can comprise different materials which can give it different physical and mechanical properties.

Referring again to FIG. 1A, in the non-everted configuration, the body frame 120 is located coaxially, laterally adjacent to and spaced apart from the leaflet frame 130, in accordance with an embodiment. The base 134 of the U-shaped portion 132 is located proximate to but not in contact with a body frame first end 127 of the body frame 120 with the U-shaped portions 132 of the leaflet frame 130 extending away from the body frame 120 and the posts 131 extending away from body frame 120 when in the non-everted configuration, as shown in FIG. 2. Note that the posts 131 are distal from the body frame first end 127 of the body frame 120. The film 160 extends across and between the U-shaped portions 132. The film 160 that extends between the U-shaped portions 132 prevents blood flow between the body frame 120 and the leaflet frame 130 when in the everted configuration. The film 160 that extends across the U-shaped portions 132 defines the leaflets 140.

Catheter Loading Profile

In the non-everted configuration the leaflet frame 130 is located coaxial with and extending away from the body frame 120, as shown in FIG. 1A. In the everted configuration the leaflet frame 130 is everted into the body frame 120 by folding about the fold region 144 to become disposed within body frame 120 while remaining coaxial therewith, as shown in FIG. 3C. The transition from a non-everted configuration to an everted configuration may be made in situ endovascularly generally at the time of deployment.

With reference to FIGS. 1D-1E, the valve 100 may be compressed into a collapsed configuration having a smaller diameter and expanded into an expanded configuration so that the valve 100 can be endovascularly delivered in the collapsed configuration and expanded upon deployment within the tissue orifice 150 as shown in FIG. 4. The leaflet frame 130 and the body frame 120 can be operable to recover circumferential uniformity when transitioning from the collapsed configuration to the expanded configuration.

The valve 100 may be mounted onto a delivery catheter either in the everted or non-everted configuration, suitable for a particular purpose. In accordance with an embodiment, the valve 100 is mounted onto a delivery catheter in the everted configuration. The valve 100 in the everted configuration has a shorter length as compared with the non-everted configuration although the profile of the valve 100 in the collapsed configuration may be determined in part by the thickness of the leaflet frame 130 being within the body frame 120.

In accordance with another embodiment, the valve 100 is mounted onto a delivery catheter in the non-everted configuration. The valve 100 being in the non-everted configuration may have a longer length as compared with the everted configuration although the profile of the valve 100 in the collapsed configuration is no longer determined in part by the thickness of the leaflet frame 130 which resides outside of the body frame 120. Therefore, the valve 100 in the non-everted configuration may have a smaller profile when mounted and compressed onto a delivery catheter. In other words, the valve 100 in the non-everted configuration can collapse to a smaller diameter onto a delivery catheter in comparison to the valve 100 that is in the everted configuration.

Referring again to FIG. 1A, in the non-everted configuration, the body frame 120 is located coaxially, laterally adjacent to and spaced apart from the leaflet frame 130, in accordance with an embodiment. The base 134 of the U-shaped portion 132 is located proximate to but not in contact with a body frame first end 127 of the body frame 120 with the U-shaped portions 132 of the leaflet frame 130 extending away from the body frame 120 and the posts 131 extending away from body frame 120 when in the non-everted configuration, as shown in FIG. 2.

It is noted that the leaflet frame 130 does not touch the body frame 120. The space between the body frame 120 and the leaflet frame 130 defines a fold region 144 of the valve 100 when bridged with film 160. The fold region 144 in combination with the non-contact between the body frame 120 and the leaflet frame 130, among other things, allows for articulation (as in a joint) of the valve 100 about the fold region when the valve 100 is mounted onto a delivery catheter and during delivery to the implantation site in the non-everted configuration.

Everted Leaflet Frame Engagement

In accordance with an embodiment, after the leaflet frame 130 is everted into the body frame 120, the leaflet frame 130 may be urged against the body frame inner surface 129 to achieve a final operational configuration. In accordance with an embodiment, the leaflet frame 130 has a spring bias towards the everted configuration wherein the leaflet frame 130 engages the body frame 120 in biased urging engagement.

In accordance with an embodiment, in the everted configuration the posts 131 abut the body frame inner surface 129 of the body frame 120, as shown in FIG. 1C. In accordance with an embodiment, the posts 131 are held adjacent to the body frame inner surface 129 by a spring bias of the leaflet frame 130. In accordance with another embodiment, the posts 131 are held in urging engagement with the body frame inner surface 129 by a spring bias of the leaflet frame 130. In accordance with yet another embodiment, the posts 131 are coupled with the body frame inner surface 129 by an engagement element (not shown) defined by the body frame 120.

In accordance with an embodiment, as shown in FIGS. 1C and 3C, the posts 131 are held adjacent to the body frame inner surface 129 by a spring bias of the leaflet frame 130 and further aligned by the engagement of the posts 131 lying within a valley 128 defined by the body frame 120. The valley 128 is operable to direct the post 131 towards the apex of the valley 128 so as to preferentially position the post 131 with respect to the body frame 120. It is understood that the posts may lie entirely within the body frame 120, or at least partially extending from and outside of the body frame 120.

The engagement of the posts 131 of the leaflet frame 130 with the body frame 120 provides support to the leaflet frame 130 to a greater extent than wherein the leaflet frame 130 is unsupported by the body frame 120. The engagement of the posts 131 with the body frame 120 allows for the transfer of loading on the leaflet 140 to the leaflet frame 130 and then to the body frame 120. In accordance with an embodiment, substantially the entire leaflet frame 130 is in urging engagement with the body frame inner surface 129. It is anticipated that the degree of engagement of the leaflet frame 130 with the body frame 120 will determine the degree of support provided on the leaflet frame 130 by the body frame 120, which may be predetermined for a particular purpose.

In other embodiments, the posts 131 are not held in engagement with the body frame inner surface 129 so as to allow inward flexing of the posts 131 under the loading of the leaflet 140 during valve operation, particularly when closing or closed. Flexing of the posts 131 may ensure that the leaflet free edges 142 coapt to form a tight seal when closed.

In embodiments of the valve 100, the inclusion of a body frame 120 and a leaflet frame 130 provides a means for providing different physical properties for each of the body frame 120 and the leaflet frame 130 suitable for a particular purpose. In accordance with an embodiment, the body frame 120 is generally inelastic as compared with the leaflet frame 130. The body frame 120, when expanded to engage the tissue orifice 150, as shown in FIG. 4, is rigid enough to remain in urging engagement with the tissue orifice 150 and to not significantly recoil to a smaller diameter or deform under physiological loading.

The physical properties of the body frame 120 and the leaflet frame 130 depends, in part, on the size, shape, thickness, material property of the body frame 120 and the leaflet frame 130 as well as the different physical properties and number of layers or wrappings of the film 160.

Clasp and/or Engagement Element

In accordance with an embodiment, one or more clasps (not shown) or some other similar engagement mechanism can secure the post 131 to the body frame 120 and add a predetermined amount of structural rigidity to the leaflet frame 130. As such, forces on the leaflet frame 130 may at least partially be transferred or distributed to the body frame 120. In this regard, the clasp comprises any structure configured to interlock, connect, fasten, or otherwise hold the leaflet frame 130 and body frame 120 together. The clasp connecting the leaflet frame 130 to the body frame 120 is operable to transfer at least some of the forces on the leaflet frame 130 to the body frame 120.

Leaflet Film

The biocompatible material that makes up the leaflet 140 can comprise any biological tissue or synthetic, biocompatible materials sufficiently compliant and flexible, such as a biocompatible polymer. In an embodiment, the leaflet 140 comprises a biocompatible polymer that is combined with an elastomer, referred to as a composite. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore, as shown in the scanning electron micrograph image in FIG. 9A, in accordance with an embodiment. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5. Embodiments of expanded fluoropolymer membrane provided herein contain a majority of fibrils having a diameter that is less than about 1 µm. Other embodiments of expanded fluoropolymer membrane provided herein contain a majority of fibrils having a diameter that is less than 0.1 µm. The embodiments provided herein recognize that a membrane comprising fibrils the majority of which are less than about 1 to beyond less than about 0.1 µm provide a significant improvement to, at least, but not limited to, the durability and lifetime of the heart valve when used as leaflet material. Embodiments of expanded fluoropolymer membrane provided herein may have a mean flow pore sizes of less than about 5 µm, less than about 1 µm, and less than about 0.10 µm, in accordance with embodiments.

In another embodiment, the expanded fluoropolymer membrane has a microstructure of substantially only fibrils, as is generally taught by U.S. Pat. No. 7,306,729, to Bacino, as shown in the scanning electron micrograph image in FIG. 9B, in accordance with an embodiment. FIG. 9C is a higher magnification of the scanning electron micrograph image in FIG. 9B and more clearly shows the homogeneous microstructure having substantially only fibrils. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5 \times 10^5$ $MPa^2$, and/or a ratio of matrix tensile strengths in two orthogonal directions of less than 4, and possibly less than 1.5. Embodiments of expanded fluoropolymer membrane provided herein contain a majority of fibrils having a diameter that is less than about 1 µm. Other embodiments of expanded fluoropolymer membrane provided herein contain a majority of fibrils having a diameter that is less than about 0.1 µm. The embodiments provided herein recognize that a membrane comprising fibrils the majority of which are less than about 1 to beyond less than about 0.1 µm provide a significant improvement to, at least, but not limited to, the durability and lifetime of the heart valve when used as leaflet material. Embodiments of expanded fluoropolymer membrane provided herein may have a mean flow pore sizes of less than about 5 µm, less than about 1 µm, and less than about 0.10 µm, in accordance with embodiments.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 µm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 µm and a mass per area of about 4.1 $g/m^2$.

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium that may be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Other Considerations

In accordance with an embodiment, the valve 100 can be configured to prevent interference with a heart conduction system by not covering the bundle branch in the left ventricle when implanted, such as might be encountered with an aortic valve replacement procedure. For example, the valve 100 can comprise a length of less than about 25 mm or less than about 18 mm. The valve 100 can also comprise an aspect ratio of less than one, wherein the ratio describes the relationship between the length of the valve 100 to the expanded, functional diameter. However, the valve 100 can be constructed at any length and, more generally, any desirable dimension.

In a collapsed state, the valve 100 can have a collapsed profile that is less than about 35% of the expanded profile. For example, the valve 100 comprising a 26 mm expanded diameter can have a collapsed diameter of less than about 8 mm, or less than about 6 mm. The percent difference in diameter is dependent on dimensions and materials of the valve 100 and its various applications, and therefore, the actual percent difference is not limited by this disclosure.

The valve 100 can further comprise a bio-active agent. Bio-active agents can be coated onto a portion or the entirety of the film 160 for controlled release of the agents once the valve 100 is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Delivery System

In an embodiment, with reference to FIGS. 4, 5A-5C, a valve delivery system 500 comprises a valve 100 having a collapsed configuration and an expanded configuration as previously described and an elongated flexible catheter 480, such as a balloon catheter, configured to endovascularly deploy the valve 100. The catheter 480 can comprise a balloon to expand the valve 100 and/or if required, to touch up the valve 100 to ensure proper seating. The valve 100 can be mounted to the distal section of the catheter 480 for delivery through the vasculature. In order to hold the valve in a collapsed configuration on the catheter 480, the valve delivery system may further comprise a removable sheath 482 to closely fit over the transcatheter valve 100.

Figure 5A:
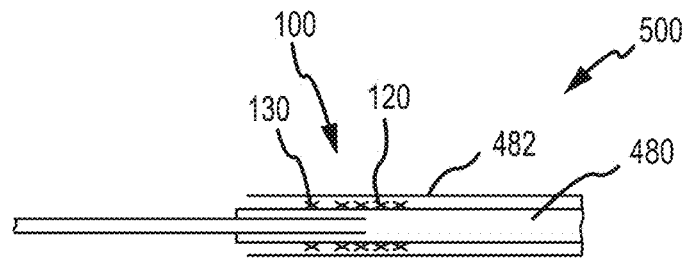
FIG. 5A is a cross-sectional view of an embodiment of the two piece valve as mounted on a delivery catheter.
Figure 5B:
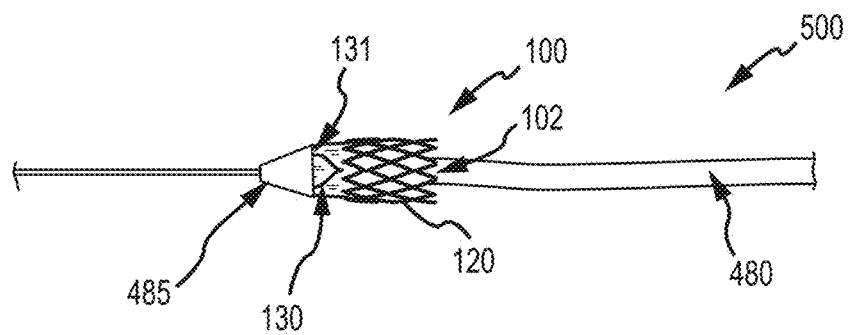
FIG. 5B is a side view of an embodiment of an everter.
Figure 5C:
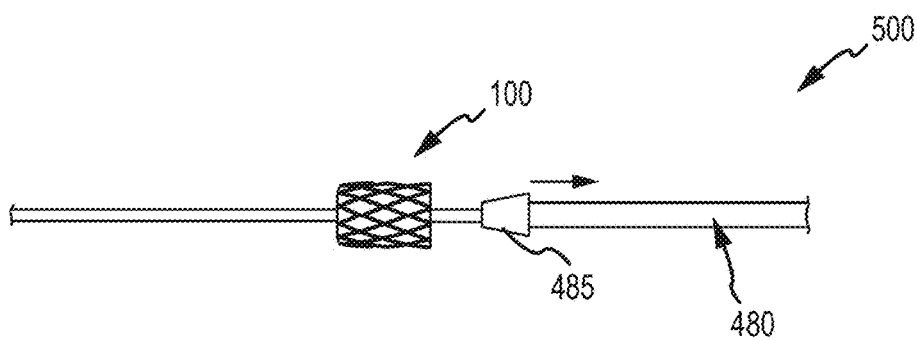
FIG. 5C is a side view of the embodiment of the everter of FIG. 5B.

A valve delivery system 500 is operable to endovascularly transition the valve 100 from a non-everted configuration to an everted configuration. For example, delivery system 500 comprises an everter 485 as shown in FIGS. 5B-5C. The everter 485 comprises any mechanism to facilitate the transition from a non-everted configuration to an everted configuration. In one embodiment, the everter 485 is configured to fit over the posts 131 of the body frame 120 while in a non-everted configuration. The everter 485 is moveable between a distal position, shown in FIG. 5B, to a proximal position, shown in FIG. 5C, relative to the valve 100, which thereby moves the leaflet frame 130 from the extended position to the everted position. The everter 485 can comprise an annular or funnel-shaped structure that radially compresses the posts 131. The everter 485 can be tethered to an elongate member that extends through the valve orifice 102 of the valve 100 and is accessible by a clinician to facilitate eversion. The above describes one embodiment; however, any device of any configuration can be used to facilitate eversion.

A method of delivery can comprise the steps of radially compressing an everted valve into its collapsed configuration onto the distal end of an elongate flexible catheter having proximal and distal ends; delivering the valve to a tissue orifice, such as a native aortic valve orifice, via a transfemoral or transapical route, and expanding the valve into the tissue orifice. The valve can be expanded by inflating a balloon.

A method of delivery can comprise the steps of radially compressing an evertable valve, while in a non-everted configuration, into its collapsed configuration, onto the distal section of an elongated flexible catheter having proximal and distal ends. A restraint, which can be connected to a tether that passes through the orifice of valve and the lumen of the catheter, is fitted around the posts of the valve. The valve is then delivered to a native valve orifice, such as a native aortic valve orifice, via a route of delivery and expanded into the native orifice. The route of delivery can comprise a transfemoral or transapical route. The valve can be expanded by inflating a balloon. Next, a clinician will evert a leaflet frame of the valve by axially displacing the restraint in a distal to proximal location. The leaflet frame can then be connected to the body frame by securing the posts into the clasps on the body frame.

Surgical Embodiments

It is appreciated that the embodiments of the valve 100 may be surgically implanted rather than using transcatheter techniques. Embodiments of a surgically implanted valve 100 may be substantially the same as those described above, with the addition of a sewing cuff about a body frame outer surface 127 in accordance with an embodiment. The sewing cuff, which is well known in the art, is operable to provide structure that receives suture for coupling the valve 100 to an implant site, such as the tissue orifice. The sewing cuff may comprise any suitable material, such as, but not limited to, double velour polyester. The sewing cuff may be located circumferentially around the body frame 120 or perivalvular depending from the base frame. The leaflet frame 130 may be everted into the body frame 120 before or after the body frame 120 is secured to the implant site.

Method of Making

Figure 6:
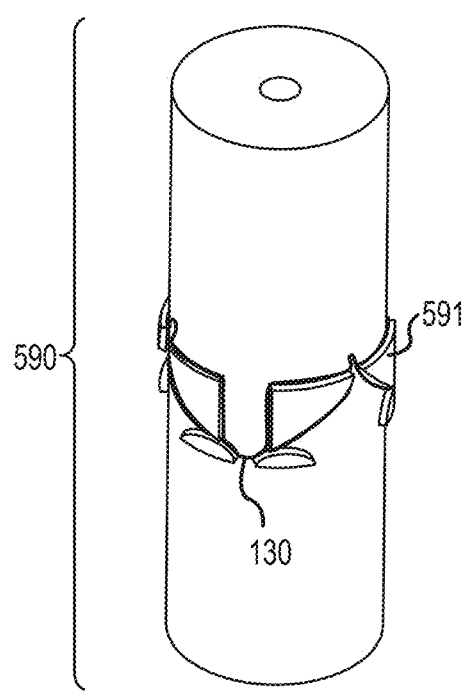
FIG. 6 is a perspective view of an embodiment of a winding jig for forming a wire into a leaflet frame.
Figures 8A, 8B:
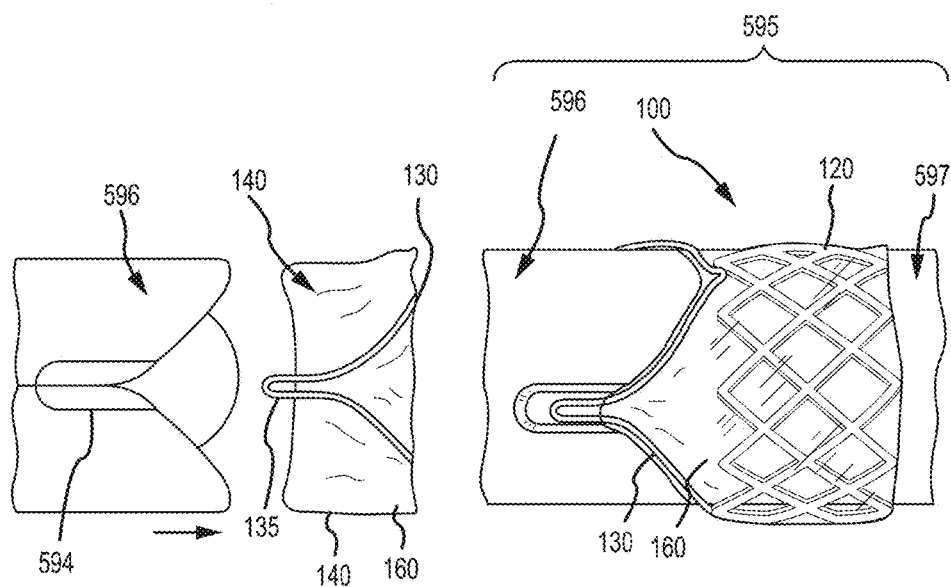
FIG. 8A is a side view of valve components on a two-piece mandrel for forming leaflets, in accordance with an embodiment.
FIG. 8B is a side view of the two-piece mandrel for forming leaflets of the embodiment of FIG. 8A.

Embodiments described herein also pertain to a method of making the valve embodiments as described herein. In order to make the various embodiments, a winding jig and a two-piece leaflet mandrel can be used. With reference to FIG. 6, winding jig 590 comprises a structural form defining the valve orifice of the valve and a leaflet frame guide 591 configured to facilitate the shaping of a wire into a desired leaflet frame shape. With reference to FIG. 8A-8B, two-piece mandrel 595 comprises a leaflet clamp 596 and a base mold 597 which together form the mandrel to mold a tubular membrane or composite to form the leaflets. Leaflet clamp 596 can comprise contoured grooves 594 along the seams of leaflet clamp 596 wherein the posts 131 will be placed into in order to define the desired curvature or bend in the leaflet frame 130.

With reference to FIG. 6, a method of making the leaflet frame can comprise the step of shaping a wire to form leaflet frame 130. Winding jig 590 can be used to form the leaflet frame 130 wherein wire is bent around posts and guides and then heat set.

Figure 7:
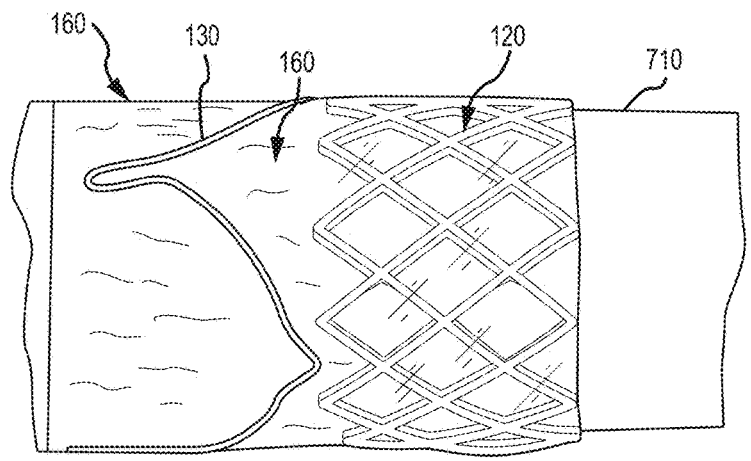
FIG. 7 is a side view of valve components on an assembly mandrel, in accordance with an embodiment.

With reference to FIGS. 7 and 8A-8B, an embodiment of a method of making valve 100 in the non-everted configuration comprises the steps of wrapping a first layer of biocompatible material such as film 160, e.g., a composite as described herein, into a tubular form about a first mandrel 710; placing the leaflet frame 130 and body frame 120 over the first layer of film 160, as shown in FIG. 7; forming a second layer of film 160 over the leaflet frame 130 and the body frame 120; thermally setting the assembly; removing the assembly from the first mandrel 710 and inserting the assembly into a two-piece mandrel 596; molding the leaflets 140 with the leaflet clamp 696 placing the leaflet clamp 696 in urging engagement with the leaflets 140; and thermal setting the leaflets 140.

EXAMPLE

By way of example, one embodiment of an evertable valve can be made as follows.

A leaflet frame was constructed by winding a nitinol wire (0.020" diameter) onto a winding jig as illustrated in FIG. 6. Once the pattern as shown in FIG. 2 was obtained, the frame was shape set in an oven set to 450° C. for 10 minutes. The leaflet frame was then exposed to a surface roughening step to improve adherence of the membrane to the frame. The frame was submersed in an ultrasonic bath of acetone for approximately five minutes. The frame surface was then subjected to a plasma treatment with methods commonly known to those having ordinary skill in the art.

FEP powder (Daikin America, Orangeburg N.Y.) was applied to the frame. The leaflet frame was then heated in a forced air oven set to 320° C. for approximately three minutes. In this way, the powder was melted and adhered as a thin coating to the entire frame. The leaflet frame was removed from the oven and left to cool to room temperature.

A body frame was laser cut from a tube of 316 stainless steel having a wall thickness of about 0.5 mm (0.02"), a diameter of about 2.5 cm (1.0"), and a length of 2 cm. A diamond-shaped pattern was cut into the tube to form an annular-shaped body frame shown in FIG. 2. The same surface treatment and FEP powder coating steps as described above were applied to the body frame.

A leaflet material was obtained. A membrane of ePTFE can be manufactured according to the general teachings described in U.S. Pat. No. 7,306,729 to Bacino et al. The ePTFE membrane had a mass per area of about 1.15 $g/m^2$, a bubble point of about 79.7 MPa, a thickness of about 1.016 μm, a matrix tensile strength of about 410.9 MPa in the longitudinal direction and about 315.4 MPa in the transverse direction.

A fluoroelastomer that is a copolymer comprising tetrafluoroethylene and perfluoro(methyl vinylether) as described in U.S. Pat. No. 7,462,675 to Chang, et al. was obtained. The copolymer consisted essentially of between about 65 and 70 weight percent perfluoromethyl vinyl ether and complementally about 35 and 30 weight percent tetrafluoroethylene.

This copolymer was dissolved in Novec HFE7500 (3M, St Paul, Minn.) in a 2.5% concentration. The ePTFE membrane (while being supported by a polypropylene release film) was coated with the prepared solution using a mayer bar and dried in a convection oven set to 145° C. for 30 seconds thereby creating an imbibed composite material. After two coating steps, the final ePTFE/fluoroelastomer or composite material had a mass per area of approximately 4.08 $g/m^2$, 28.22% fluoropolymer by weight, a dome burst strength of 15.9 KPa, and a thickness of 1.89 μm.

Fifteen layers of the composite material were wrapped around the combined 25 mm diameter aluminum mandrel assembly shown in FIG. 7 with the elastomer rich side facing away from the mandrel. The fifteen layers of composite material were each circumferentially wrapped around the mandrel so as to orient the transverse direction of the composite along the longitudinal axis of the mandrel. The leaflet frame was everted from its wire wound condition, then coaxially positioned on the mandrel, as illustrated in FIG. 8A. The body frame was then positioned onto the mandrel as shown in FIG. 7.

Five additional layers of composite material were wrapped around the leaflet frame and body frame with the elastomer rich side of each layer facing toward the leaflet frame and the body frame.

The assembly was then circumferentially wrapped with a polyimide release film sacrificial layer. The assembly was heated in a forced air oven set to about 280° C. for about 30 minutes. The assembly was removed from the oven and water quenched. The sacrificial layer was removed thereby exposing the valve. Excess leaflet material was trimmed to form the free edge with scissors from the top of the frame posts to the common triple point of each leaflet as shown in FIGS. 1A and 8A to create three commissures or coapting surface regions. The non-everted frame assembly was removed from the tooling.

The leaflets were then formed to a predetermined shape by positioning the leaflet clamp 596 as shown in FIGS. 8A and 8B and subsequently closing the leaflet clamp 596 against the leaflets. The combined mandrel assembly were then thermal treated to set the leaflet shape.

Testing Methods

It should be understood that although certain methods and equipment are described below, any method or equipment determined suitable by one of ordinary skill in the art may be alternatively utilized.

Bubble Point and Mean Flow Pore Size

Bubble point and mean flow pore size were measured according to the general teachings of ASTM F31 6-03 using a capillary flow Porometer, Model CFP 1500AEXL from Porous Materials, Inc., Ithaca N.Y., USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. The test fluid was isopropyl alcohol. Using the Capwin software version 7.73.012 the following parameters were set as specified in the table below. As used herein, mean flow pore size and pore size are used interchangeably.

| Parameter | Set Point |
| --- | --- |
| Maxflow (cm³/m) | 200000 |
| Bublflow(cm³/m) | 100 |
| F/PT (old bubltime) | 50 |
| Minbpress (PSI) | 0 |
| Zerotime (sec) | 1 |
| V2incr (cts) | 10 |
| Preginc (cts) | 1 |
| Pulse delay (sec) | 2 |
| Maxpre (PSI) | 500 |
| Pulse width (sec) | 0.2 |
| Mineqtime (sec) | 30 |
| Presslew (cts) | 10 |
| Flowslew (cts) | 50 |
| Eqiter | 3 |
| Aveiter | 20 |
| Maxpdif (PSI) | 0.1 |
| Maxfdif (PSI) | 50 |
| Sartp (PSI) | 1 |
| Sartf (cm³/m) | 500 |

Presence of Elastomer within the Pores

The presence of elastomer within the pores can be determined by several methods known to those having ordinary skill in the art, such as surface and/or cross section visual, or other analyses. These analyses can be performed prior to and after the removal of elastomer from the composite.

Diameter of Fibrils

Figure 9A:
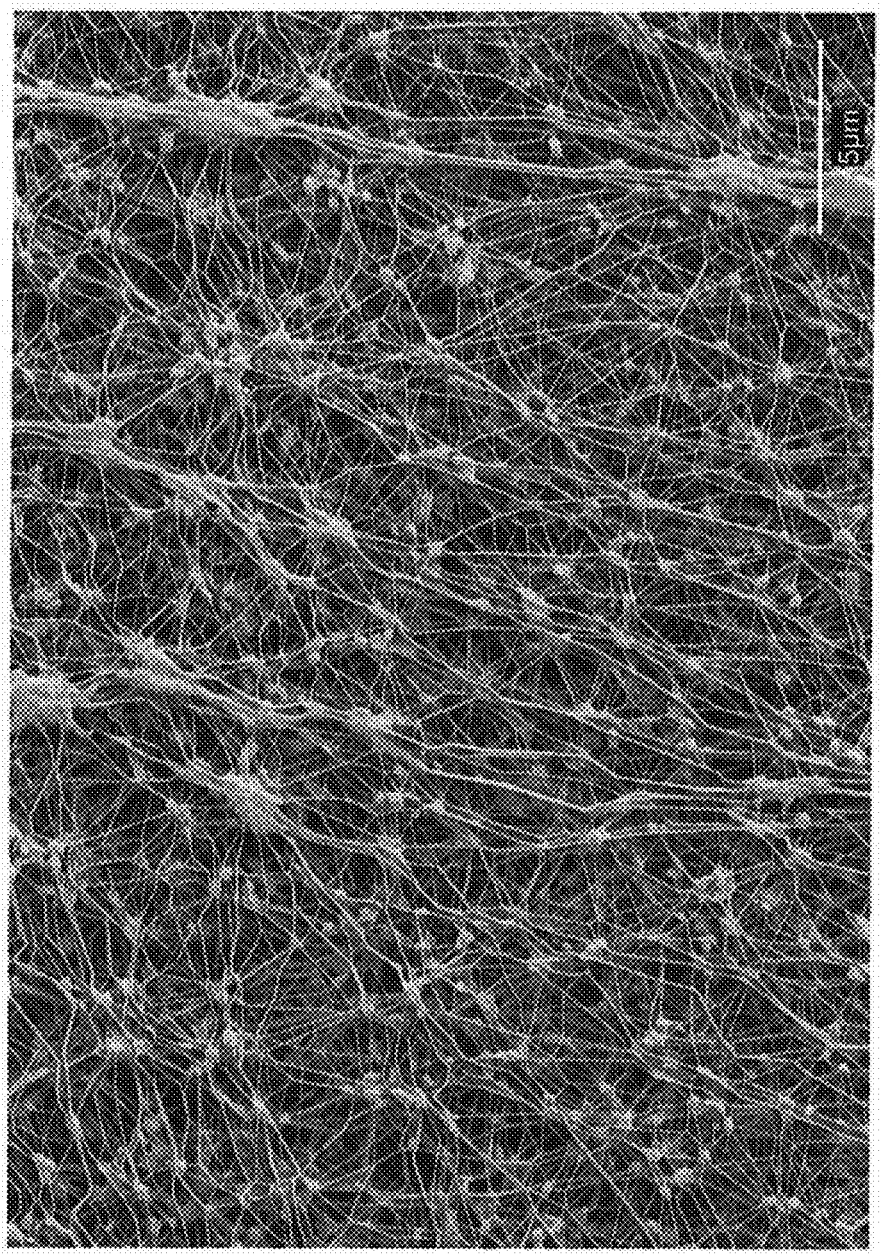
FIG. 9A is a scanning electron micrograph image of ePTFE, in accordance with an embodiment.
Figure 9B:
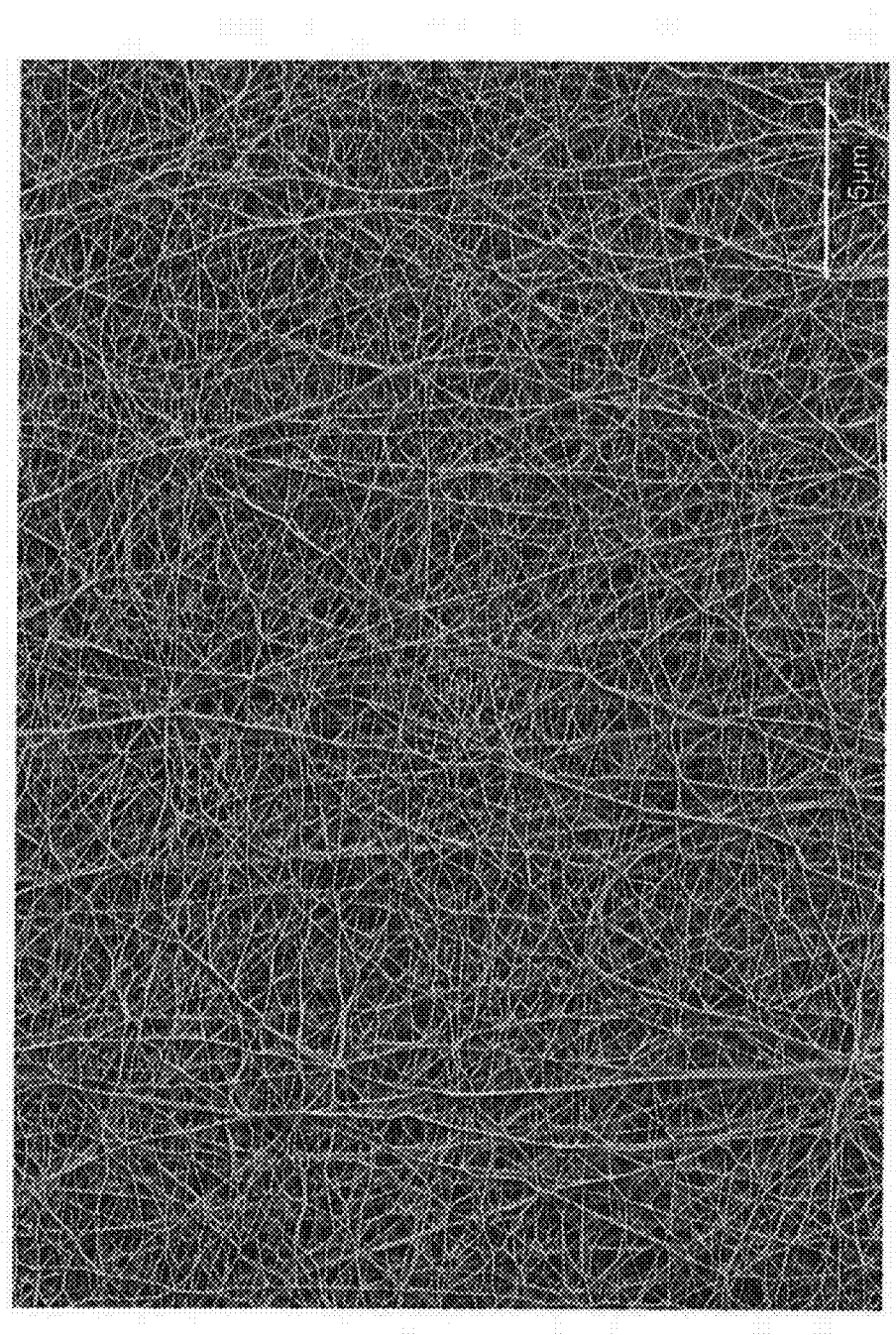
FIG. 9B is a scanning electron micrograph image of ePTFE, in accordance with another embodiment.
Figure 9C:
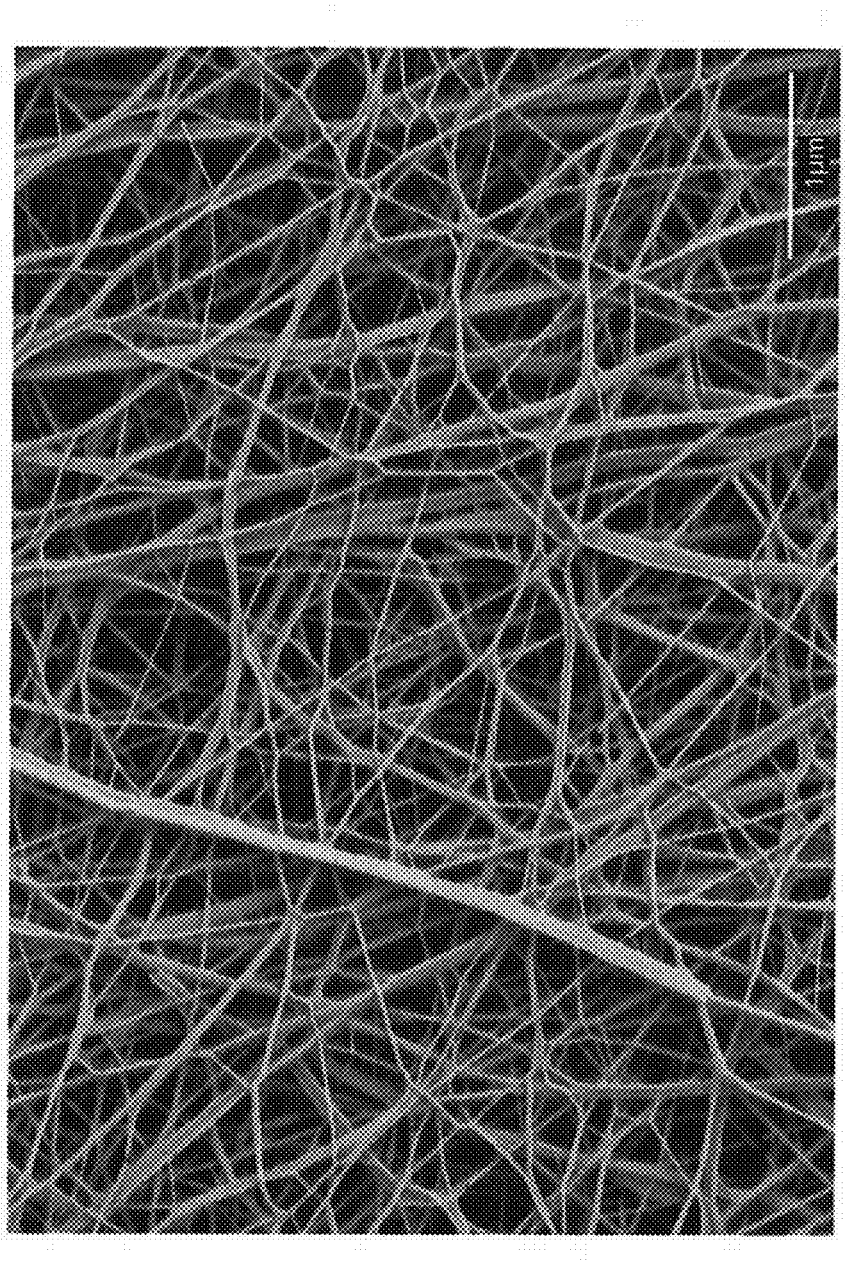
FIG. 9C is a higher magnification of the scanning electron micrograph image of ePTFE of FIG. 9B.

The average diameter of the fibrils was estimated by examining micrographs that were obtained having at a magnification suitable for showing numerous fibrils, such as the scanning electron microscopy (SEM) micrographs of FIGS. 9A-C. In the case of a composite material, it may be necessary to extract the elastomer or other material that may be filling the pores, by any suitable means, to expose the fibrils.

Mass, Thickness, and Density of ePTFE Membranes

Membrane thickness was measured by placing the membrane between the two plates of a Käfer FZ1000/30 thickness snap gauge Käfer Messuhrenfabrik GmbH, Villingen-Schwenningen, Germany. The average of the three measurements was reported.

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho=m/(w*l*t)$, in which: $\rho$=density (g/cm³), m=mass (g), w=width (cm), l=length (cm), and t=thickness (cm). The average of three measurements was reported.

Matrix Tensile Strength (MTS) of ePTFE Membranes

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the Käfer FZ1000/30 snap gauge; alternatively, any suitable means for measuring thickness may be used. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), where the bulk density of the PTFE was taken to be about 2.2 g/cm³.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed:

1. A transcatheter valve having a multi-part frame, the transcatheter valve comprising:
   a multi-part frame including,
      a body frame defining a generally tubular shape;
      a leaflet frame defining a generally annular shape and coaxially disposed relative to, extending away and spaced apart from the body frame defining a fold region therebetween, the leaflet frame defining a plurality of U-shaped portions each defining a base and a plurality of posts, the base of each U-shaped portion being located proximate to but not in contact with a body frame first end of the body frame with the U-shaped portions of the leaflet frame extending away from the body frame and the posts extending away from body frame, the posts being distal from the body frame first end; and
   a film extending across and between the body frame and leaflet frame bridging the fold region and coupling the body frame to the leaflet frame, the leaflet frame and film defining a plurality of leaflets disposed within each U-shaped portion, each leaflet having a leaflet free edge, wherein the leaflet frame is operable to evert along the fold region so as to dispose the leaflet frame at least partially within the body frame and defining a valve wherein the leaflet free edges abut adjacent leaflet free edges and are moveable between an open and closed position.

2. The transcatheter valve of claim 1, wherein the body frame is more stiff than the leaflet frame.

3. The transcatheter valve of claim 2, wherein the film comprises a polymeric material.

4. The transcatheter valve of claim 3, wherein the film comprises a laminate.

5. The transcatheter valve of claim 4, wherein the laminate has more than one layer of a fluoropolymer membrane.

6. The transcatheter valve of claim 3, wherein the film comprises a composite material having at least one fluoropolymer membrane layer having a plurality of pores and an elastomer present in substantially all of the pores of at least one layer of fluoropolymer membrane.

7. The transcatheter valve of claim 6, wherein the composite material comprises less than about 80% fluoropolymer membrane by weight.

8. The transcatheter valve of claim 6, wherein the elastomer comprises (per)fluoroalkylvinylethers (PAVE).

9. The transcatheter valve of claim 6, wherein the elastomer comprises a copolymer of tetrafluoroethylene and perfluoromethyl vinyl ether.

10. The transcatheter valve of claim 6, wherein the fluoropolymer membrane com prises ePTFE.

11. The transcatheter valve of claim 2, wherein the body frame comprises a non-shape memory material.

12. The transcatheter valve of claim 2, wherein the body frame is substantially symmetrical about a plane perpendicular to a central axis.

13. The transcatheter valve of claim 2, wherein the body frame comprises an open framework operable to allow the body frame to be compressed to a collapsed configuration and expanded between different diameters.

14. The transcatheter valve of claim 13, wherein the body frame is a generally tubular member defining a generally open pattern of apertures operable to allow the body frame to be compressed and expanded between different diameters.

15. The transcatheter valve of claim 13, wherein the collapsed configuration has a collapsed profile less than about 6 mm.

16. The transcatheter valve of claim 2, wherein an aspect ratio of a length of the transcatheter valve to an expanded diameter of the transcatheter valve is less than 1.

17. The transcatheter valve of claim 2, wherein the body frame is less than about 20 mm in length.

18. The transcatheter valve of claim 2, wherein the leaflet frame comprises a shape-memory material.

19. The transcatheter valve of claim 2, wherein the leaflet frame comprises a metallic material.

20. The transcatheter valve of claim 2, wherein the leaflet frame is formed from a wire.

21. The transcatheter valve of claim 2, wherein the at least a portion of the leaflet frame is held adjacent to a body frame inner surface by a spring bias of the leaflet frame.

22. The transcatheter valve of claim 2, wherein the transcatheter valve is balloon expandable.

23. A transcatheter valve having a multi-part frame, the transcatheter valve comprising:
 a body frame defining a body frame lumen;
 a leaflet frame, the leaflet frame defining a first position in which the body frame extends coaxially, adjacent to and spaced apart from the leaflet frame; and
 a film assembly including a first portion defining a plurality of leaflets connected to the leaflet frame and a second portion extending between the leaflet frame and the body frame and defining a fold region, the leaflet frame being evertible about the fold region from the first position to a second position in which the leaflet frame is at least partially coaxially disposed within the body frame lumen.

24. The transcatheter valve of claim 23, wherein the body frame comprises a clasp configured to hold the leaflet frame in the second position following eversion of the leaflet frame to the second position.

25. The transcatheter valve of claim 23, wherein the film sandwiches the body frame and the leaflet frame.

26. The transcatheter valve of claim 23, the body frame having a body frame inner surface defining the body frame lumen, wherein the at least a portion of the leaflet frame is held adjacent to a body frame inner surface by a spring bias of the leaflet frame.

27. The transcatheter valve of claim 23, wherein the body frame comprises an open framework operable to allow the body frame to be compressed to a collapsed configuration and expanded between different diameters or the body frame is a generally tubular member defining a generally open pattern of apertures operable to allow the body frame to be compressed and expanded between different diameters.

28. The transcatheter valve of claim 27, wherein the body frame is more stiff than the leaflet frame.

29. The transcatheter valve of claim 23, wherein the body frame is substantially symmetrical about a plane perpendicular to a central axis.

30. The transcatheter valve of claim 23, wherein the body frame is substantially axially stiff.

31. A transcatheter valve having a multi-part frame, the transcatheter valve comprising:
 a first frame having an annular shape and being expandable from a first, compact diameter when the first frame is in a compacted state to a second, enlarged diameter when the first frame is in an expanded state;
 a second frame having an annular shape and being expandable from a first, compact diameter when the second frame is in a compacted state to a second, enlarged diameter when the second frame is in an expanded state, wherein the second, enlarged diameter of the second frame is larger than the second, enlarged diameter of the first frame; and
 a bridge region coupling the first frame to the second frame;
 the transcatheter valve having a first delivery state in which the first frame is coaxial with, but longitudinally spaced from the second frame with the bridge region extending longitudinally between the first frame and the second frame and an everted state in which the bridge region is folded over into the second frame and the first frame is coaxial with the second frame with at least a portion of the first frame disposed within the second frame.

32. The transcatheter valve of claim 31, wherein the first frame has a different radial stiffness than that of the second frame.

33. A transcatheter valve comprising:
 a multi-part frame defining a flow lumen through which fluid is able to selectively flow, the multi-part frame including,
  an outer support portion having a generally tubular shape defining a first lumen,
  an evertible support portion having a generally tubular shape, and
  a flexible bridge material coupling the evertible support portion to the outer support portion, such that the evertible support portion is transitionable from a first, laterally adjacent position relative to the outer support portion and a second, everted position in which the evertible support portion is at least partially located within the first lumen of the outer support portion; and a plurality of leaflets coupled to the multi-part frame, each leaflet being moveable between an open position and closed position to selectively block and unblock the flow lumen of the multi-part frame.

34. The transcatheter valve of claim 33, wherein the flexible bridge material is folded over a distal end of the outer support portion of the multi-part frame when the evertible support portion is transitioned to the everted position.

35. The transcatheter valve of claim 33, wherein when the evertible support portion is in the first, laterally adjacent position the transcatheter valve has a smaller compressed profile when mounted and compressed onto a delivery catheter in comparison to a compressed profile that is achievable when the evertible support portion is in the second, everted position.

36. The transcatheter valve of claim 33, wherein the outer support portion has a different stiffness than the evertible support portion.

37. The transcatheter valve of claim 33, wherein the transcatheter valve is compressed onto a delivery catheter in a collapsed configuration with the support portion located in the first, laterally adjacent position.

38. A transcatheter valve comprising:
a multi-part frame, including:
a body frame having a generally tubular shape defining a body frame lumen, and
a leaflet frame having a generally annular shape defining a plurality of bases and a plurality of posts, the body frame extending coaxially, adjacent to and spaced apart from the leaflet frame; and
a plurality of leaflets coupled to the plurality of bases between the plurality of posts,
wherein the multi-part frame is configured to be everted into itself from an axially extended, non-everted configuration in which the leaflet frame is spaced axially apart from the body frame to an everted configuration in which the leaflet frame is received at least partially within the lumen of the body frame.

39. The transcatheter valve of claim 38, further comprising a film that extends across and between the body frame and leaflet frame bridging a fold region between the leaflet frame and the body frame and coupling the body frame to the leaflet frame, wherein the multi-part frame is operable to evert along the fold region so as to dispose the leaflet frame at least partially within the body frame.

40. The transcatheter valve of claim 38, wherein the when the multi-part frame is in the non-everted configuration the transcatheter valve has a smaller compressed profile when mounted and compressed onto a delivery catheter in comparison to a compressed profile that is achievable when the multi-part frame is in the everted configuration.

* * * * *